(12) United States Patent  
Londborg et al.

(10) Patent No.: US 10,828,489 B2  
(45) Date of Patent: Nov. 10, 2020

(54) WEARABLE CASE FOR HEARING DEVICE AND METHODS FOR USING THE SAME

(71) Applicant: Advanced Bionics AG, Staefa (CH)

(72) Inventors: Mark Londborg, West Hills, CA (US); Mo C. Chan, Valencia, CA (US)

(73) Assignee: Advanced Bionics AG, Staefa (CH)

( * ) Notice: Subject to any disclaimer, the term of this patent is extended or adjusted under 35 U.S.C. 154(b) by 90 days.

(21) Appl. No.: 16/207,085

(22) Filed: Nov. 30, 2018

(65) Prior Publication Data

US 2020/0171306 A1  Jun. 4, 2020

(51) Int. Cl.
*A61N 1/36* (2006.01)  
*H04R 25/00* (2006.01)

(52) U.S. Cl.
CPC ....... *A61N 1/36038* (2017.08); *H04R 25/602* (2013.01); *H04R 25/65* (2013.01); *H04R 25/604* (2013.01); *H04R 2225/021* (2013.01); *H04R 2225/67* (2013.01)

(58) Field of Classification Search
CPC .. A61N 1/36038; H04R 25/65; H04R 25/602; H04R 25/604; H04R 2225/021; H04R 2225/67
See application file for complete search history.

(56) References Cited

U.S. PATENT DOCUMENTS

| | | | |
|---|---|---|---|
| 6,758,338 B2* | 7/2004 | Lien | B65D 25/10 206/534 |
| 8,177,112 B1* | 5/2012 | Crawford | A45F 5/02 224/666 |
| 8,180,083 B2* | 5/2012 | Campbell | H04R 25/65 381/189 |
| 2007/0286443 A1 | 12/2007 | Gommel et al. | |
| 2015/0249897 A1 | 9/2015 | Darley et al. | |
| 2016/0142835 A1 | 5/2016 | Walsh et al. | |
| 2016/0269838 A1 | 9/2016 | Harte et al. | |
| 2016/0296755 A1 | 10/2016 | Van Der Borght et al. | |
| 2017/0099551 A1 | 4/2017 | Walsh et al. | |

FOREIGN PATENT DOCUMENTS

CN   203027392   6/2013

* cited by examiner

Primary Examiner — Rex R Holmes  
(74) Attorney, Agent, or Firm — ALG Intellectual Property, LLC

(57) ABSTRACT

A wearable case for a hearing device includes a cradle member configured to receive the hearing device, and a cover member pivotally connected to the cradle member and configured to selectively pivot between an open position and a closed position. When the cover member is in the closed position, the cradle member and the cover member are configured to securely cradle the hearing device within a space defined by the cradle member and the cover member without fully enclosing an entire surface area of the hearing device. When the cover member is in the open position, the hearing device is removable from the cradle member.

20 Claims, 8 Drawing Sheets

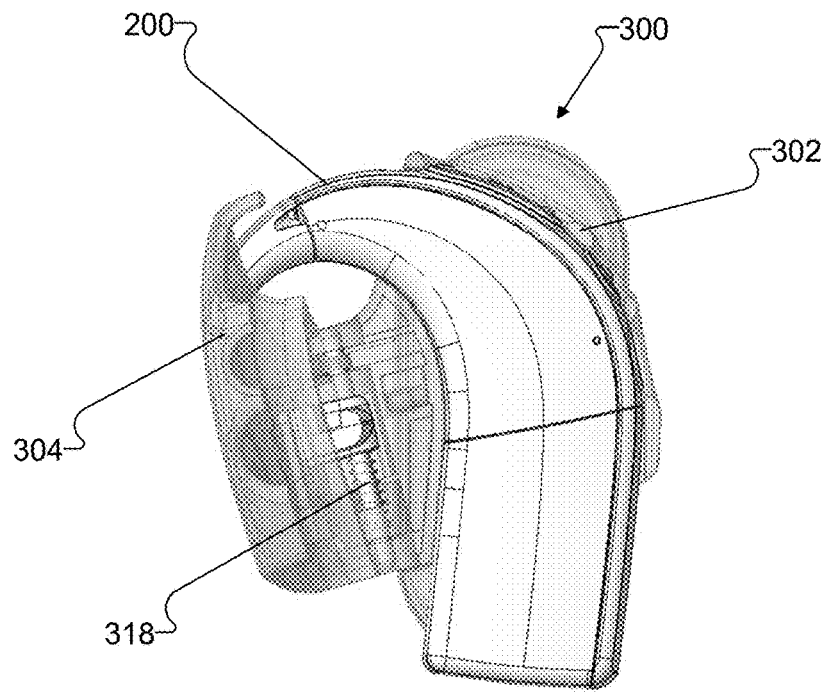
Fig. 5A
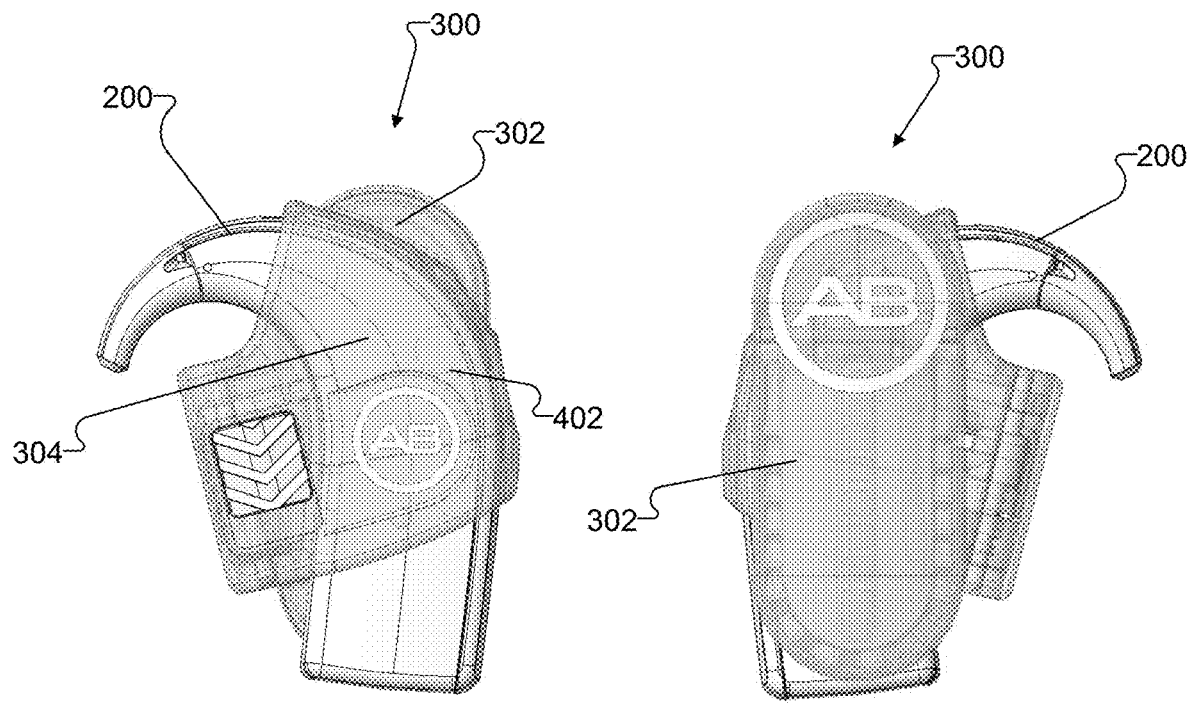
Fig. 5B     Fig. 5C

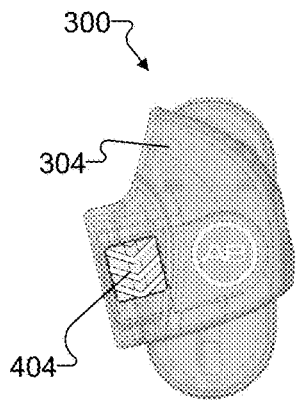 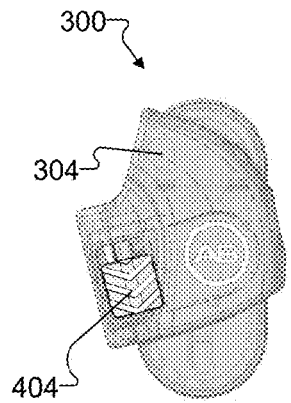 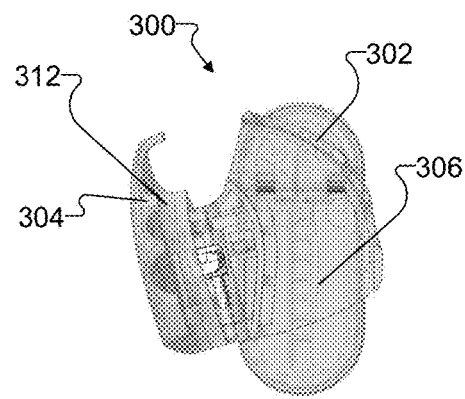
Fig. 7A  Fig. 7B  Fig. 7C
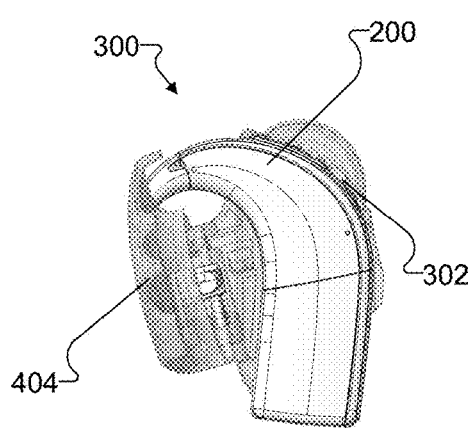 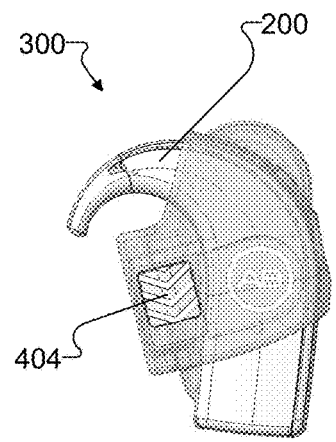
Fig. 7D  Fig. 7E

US 10,828,489 B2

WEARABLE CASE FOR HEARING DEVICE AND METHODS FOR USING THE SAME

BACKGROUND INFORMATION

A hearing device, such as a hearing aid or a sound processor included in a cochlear implant system, is typically worn behind the ear of a user. However, in some situations, it may be more convenient for a user of the hearing device to attach the hearing device to an article of clothing, such as a shirt, belt, or pants. To do this, the user may attach a clip assembly to the hearing device and then secure the clip assembly to an article of clothing.

However, conventional clip assemblies exhibit several problems when holding hearing devices. For example, some conventional clip assemblies hold the hearing device by exerting a force, such as by a spring clip, on the hearing device. Because hearing devices may have complex shapes and may be fragile and small, this force may damage the hearing device. Additionally, this force may be overcome by impacts to the clip assembly or the hearing device and thereby accidentally release the hearing device from the clip assembly. Moreover, it may be difficult or inconvenient to access the hearing device (e.g., to replace a battery of the hearing device or interact with controls on the hearing device) while the hearing device is attached to a conventional clip assembly.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

FIGS. 5A-5C show various views of the wearable case of FIGS. 3 and 4 together with the sound processor assembly of FIG. 2 according to principles described herein.

FIGS. 7A-7E illustrate an exemplary method of using the wearable case of FIGS. 3 and 4 with the sound processor assembly of FIG. 2 according to principles described herein.

DETAILED DESCRIPTION

Figure 1:
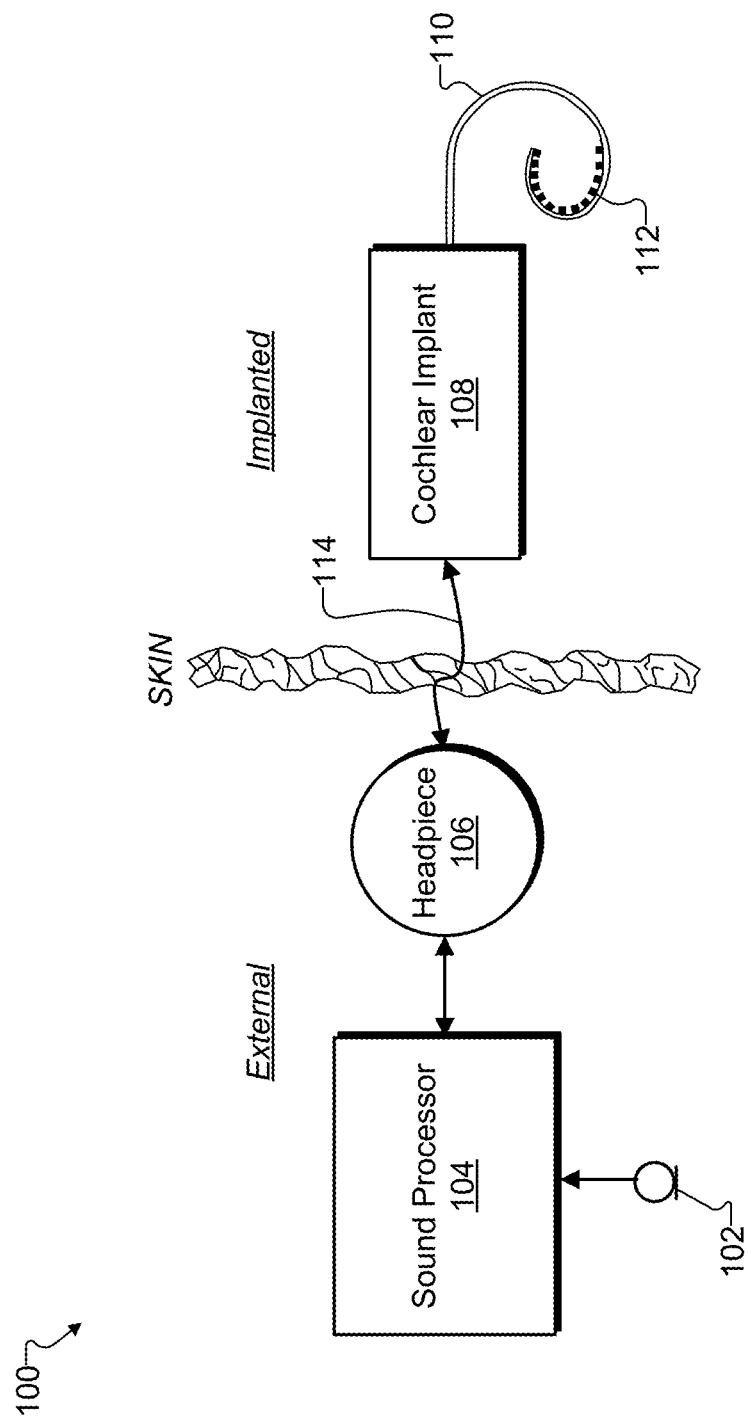
FIG. 1 illustrates an exemplary cochlear implant system according to principles described herein.

Wearable cases for a hearing device and methods of using the wearable cases are described herein. As will be described in more detail below, an exemplary wearable case includes a cradle member configured to receive a hearing device (e.g., a hearing aid, a sound processor included in a cochlear implant system, or a combination thereof). The wearable case further includes a cover member pivotally connected to the cradle member and configured to selectively pivot between an open position and a closed position. When the cover member is in the closed position, the cradle member and the cover member are configured to securely cradle the hearing device within a space defined by the cradle member and the cover member without fully enclosing an entire surface area of the hearing device. When the cover member is in the open position, the hearing device is removable from the cradle member.

The wearable case described herein securely cradles the hearing device without exerting a force (e.g., putting direct pressure) on the hearing device. In this way, damage that may be caused by exerting a force on the hearing device may be prevented. Additionally, the cover member of the wearable case may prevent accidental release of the hearing device from the wearable case when the cover member is in a closed position. Additionally, the cover member of the wearable case allows removal of the hearing device from the wearable case when the cover member is in an open position. Accordingly, the wearable case securely holds and enables release of the hearing device without causing damage to the hearing device.

Additionally, by securing the hearing device without fully enclosing an entire surface area of the hearing device, the exemplary wearable case allows access to removable and/or replaceable components of the hearing device. For example, a battery module or earhook of the hearing device may be exposed outside of the space defined by the cradle member and the cover member, even when the cover member is in a closed position and the hearing device is securely cradled inside the space. Such a configuration may allow, for example, a user to remove a depleted battery module and replace it with a charged battery module without removing the hearing device from the wearable case and without opening the cover member of the wearable case. Furthermore, since the wearable case is configured such that removable components of the hearing device are disposed outside of the space defined by the cradle member and the cover member, removable components of varying sizes may be attached to the hearing device while the wearable case securely cradles the hearing device. Accordingly, the wearable case increases convenience to a user and prevents damage to the hearing device securely cradled by the wearable case.

Various embodiments will now be described in more detail with reference to the figures. The wearable cases and methods described herein may provide one or more of the benefits mentioned above and/or various additional and/or alternative benefits that will be made apparent herein.

The wearable cases described herein may be used with any suitable medical device, such as but not limited to a hearing device. For example, the hearing device may be a sound processor included in a cochlear implant system. As such, an exemplary cochlear implant system will now be described. The described exemplary cochlear implant system is illustrative and not limiting.

FIG. 1 illustrates an exemplary cochlear implant system 100. As shown, cochlear implant system 100 may include a microphone 102, a sound processor 104, a headpiece 106 having a coil disposed therein, a cochlear implant 108, and an electrode lead 110. Electrode lead 110 may include an array of electrodes 112 disposed on a distal portion of electrode lead 110 and that are configured to be inserted into the cochlea to stimulate the cochlea after the distal portion of electrode lead 110 is inserted into the cochlea. It will be understood that one or more other electrodes (e.g., including a ground electrode, not explicitly shown in FIG. 1) may also be disposed on other parts of electrode lead 110 (e.g., on a proximal portion of electrode lead 110) to, for example, provide a current return path for stimulation current generated by electrodes 112 and to remain external to the cochlea after electrode lead 110 is inserted into the cochlea. Additional or alternative components may be included within cochlear implant system 100 as may serve a particular implementation. For example, a pre-curved electrode lead and/or a straight electrode lead may alternatively be used in connection with cochlear implant 108.

As shown, cochlear implant system 100 may include various components configured to be located external to a recipient including, but not limited to, microphone 102, sound processor 104, and headpiece 106. Cochlear implant system 100 may further include various components configured to be implanted within the recipient including, but not limited to, cochlear implant 108 and electrode lead 110.

Microphone 102 may be configured to detect audio signals presented to the user. Microphone 102 may be implemented in any suitable manner. For example, microphone 102 may include a microphone that is configured to be placed within the concha of the ear near the entrance to the ear canal, such as a T-MIC™ microphone from Advanced Bionics. Such a microphone may be held within the concha of the ear near the entrance of the ear canal by a boom or stalk that is attached to an earhook configured to be selectively attached to sound processor 104. Additionally or alternatively, microphone 102 may be implemented by one or more microphones disposed within headpiece 106, one or more microphones disposed within sound processor 104, one or more beam-forming microphones, and/or any other suitable microphone as may serve a particular implementation.

Sound processor 104 (i.e., one or more components included within sound processor 104) may be configured to direct cochlear implant 108 to generate and apply electrical stimulation (also referred to herein as "stimulation current") representative of one or more audio signals (e.g., one or more audio signals detected by microphone 102, input by way of an auxiliary audio input port, input by way of a device like the Clinical Programming Interface ("CPI") device from Advanced Bionics, etc.) to one or more stimulation sites associated with an auditory pathway (e.g., the auditory nerve) of the recipient. Exemplary stimulation sites may include, but are not limited to, one or more locations within the cochlea, the cochlear nucleus, the inferior colliculus, and/or any other nuclei in the auditory pathway. To this end, sound processor 104 may process the one or more audio signals in accordance with a selected sound processing strategy or program to generate appropriate stimulation parameters for controlling cochlear implant 108. Sound processor 104 may be included within a sound processor assembly, which may include any suitable housing (e.g., a behind-the-ear ("BTE") housing or a body-worn housing) together with one or more other components (e.g., a battery module and/or an earhook). An exemplary sound processor assembly will be described below in more detail.

In some examples, sound processor 104 may wirelessly transmit stimulation parameters (e.g., in the form of data words included in a forward telemetry sequence) and/or power signals to cochlear implant 108 by way of a wireless communication link 114 between headpiece 106 and cochlear implant 108 (e.g., a wireless link between a coil disposed within headpiece 106 and a coil physically coupled to cochlear implant 108). It will be understood that communication link 114 may include a bi-directional communication link and/or one or more dedicated uni-directional communication links.

Headpiece 106 may be communicatively coupled to sound processor 104 and may include an external antenna (e.g., a coil and/or one or more wireless communication components) configured to facilitate selective wireless coupling of sound processor 104 to cochlear implant 108. Headpiece 106 may additionally or alternatively be used to selectively and wirelessly couple any other external device to cochlear implant 108. To this end, headpiece 106 may be configured to be affixed to the recipient's head and positioned such that the external antenna housed within headpiece 106 is communicatively coupled to a corresponding implantable antenna (which may also be implemented by a coil and/or one or more wireless communication components) included within or otherwise associated with cochlear implant 108. In this manner, stimulation parameters and/or power signals may be wirelessly transmitted between sound processor 104 and cochlear implant 108 via communication link 114.

Cochlear implant 108 may include any type of implantable stimulator that may be used in association with the systems and methods described herein. For example, cochlear implant 108 may be implemented by an implantable cochlear stimulator. In some alternative implementations, cochlear implant 108 may include a brainstem implant and/or any other type of cochlear implant that may be implanted within a recipient and configured to apply stimulation to one or more stimulation sites located along an auditory pathway of a recipient.

In some examples, cochlear implant 108 may be configured to generate electrical stimulation representative of an audio signal processed by sound processor 104 (e.g., an audio signal detected by microphone 102) in accordance with one or more stimulation parameters transmitted thereto by sound processor 104. Cochlear implant 108 may be further configured to apply the electrical stimulation to one or more stimulation sites (e.g., one or more intracochlear regions) within the recipient via electrodes 112 disposed along electrode lead 110. In some examples, cochlear implant 108 may include a plurality of independent current sources each associated with a channel defined by one or more of electrodes 112. In this manner, different stimulation current levels may be applied to multiple stimulation sites simultaneously by way of multiple electrodes 112.

Figure 2A:
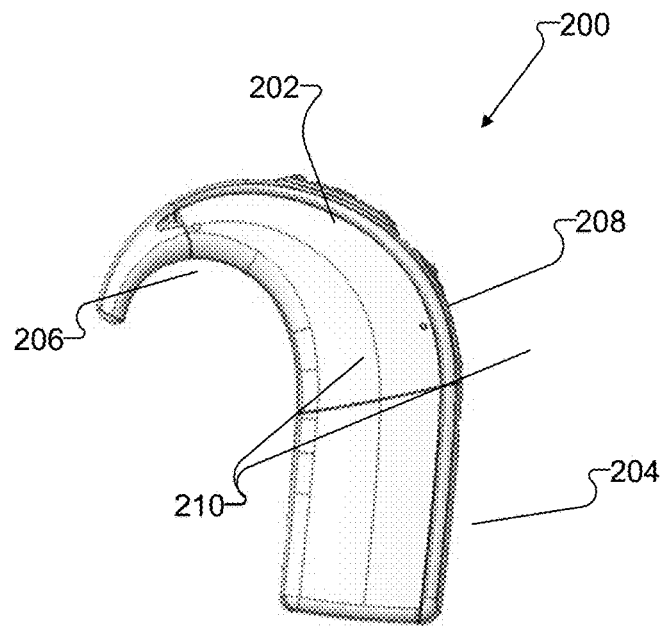
FIGS. 2A and 2B illustrate an exemplary sound processor assembly according to principles described herein.
Figure 2B:
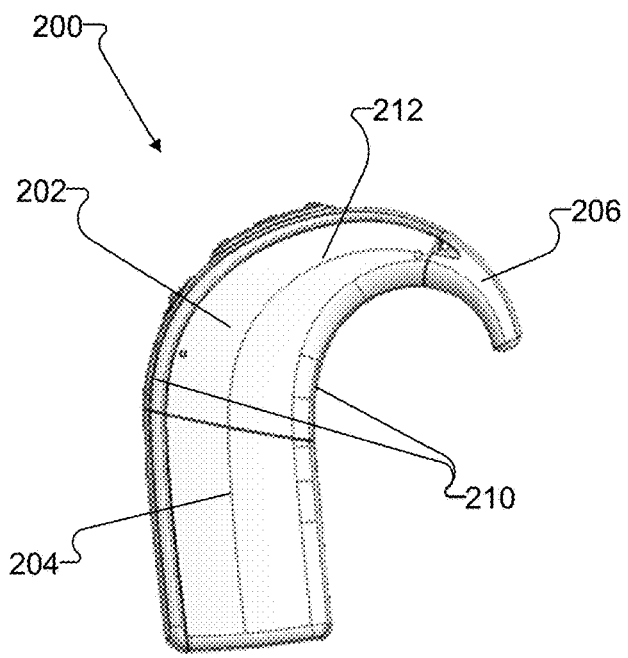

As mentioned above, sound processor 104 may be included within a sound processor assembly, such as a BTE unit configured to be worn behind an ear of a user. FIGS. 2A and 2B illustrate an exemplary sound processor assembly 200 that may house a sound processor and that may be secured by the wearable cases described herein. As shown, sound processor assembly 200 includes a sound processor module 202, a battery module 204, and an earhook 206 removably connected together.

Sound processor module 202 houses a sound processor (e.g., sound processor 104 included in cochlear implant system 100). Battery module 204 houses a battery and is removably connected to sound processor module 202 to provide electrical power to sound processor module 202 (e.g., to sound processor 104 included in sound processor module 202). Battery module 204 may be removed from sound processor module 202 to enable the user to replace or recharge the battery. Earhook 206 is removably connected to sound processor module 202. As shown in FIGS. 2A and 2B, earhook 206 is curved so as to hook around the top of the ear of the user to support sound processor assembly 200 behind the ear of the user. Earhook 206 may be removed from sound processor module 202, such as to enable the user to replace earhook 206 with an earhook having a different function.

As shown in FIG. 2A, sound processor assembly 200 has a front surface 208 (e.g., surfaces of sound processor module 202, battery module 204, and earhook 206 that face away from the user when sound processor assembly 200 is worn by the user) and side surfaces 210 (e.g., surfaces of sound processor module 202, battery module 204, and earhook 206 that intersect front surface 208). As shown in FIG. 2B, sound processor assembly 200 also has a rear surface 212 (e.g., surfaces of sound processor module 202, battery module 204, and earhook 206 that face toward the user when sound processor assembly 200 is worn by the user).

In some examples, sound processor assembly 200 (e.g., sound processor module 202, battery module 204, and/or earhook 206) may include one or more user controls (not shown in FIGS. 2A-2B) for providing input to sound processor assembly 200 (e.g., to sound processor 104). For example, user controls may allow a user to adjust volume, set an operating mode of sound processor 104, adjust a stimulation parameter, and the like. In addition to user controls, sound processor assembly 200 may also include one or more ports (not shown in FIGS. 2A-2B) for communicatively connecting one or more external devices (e.g., a mobile phone, a media player, an audio device, etc.) to sound processor assembly 200.

While sound processor assembly 200 is configured to be worn behind the ear, a user may desire (e.g., for comfort, convenience, or personal preference) to wear sound processor assembly 200 in a configuration other than behind the ear. To this end, sound processor assembly 200 may be securely cradled in a wearable case that may be removably attached (e.g., clipped) to clothing (e.g., a shirt, a belt, pants, a backpack, etc.), parts of the user's body other than the ear, or any other object desired by the user.

Figure 3:
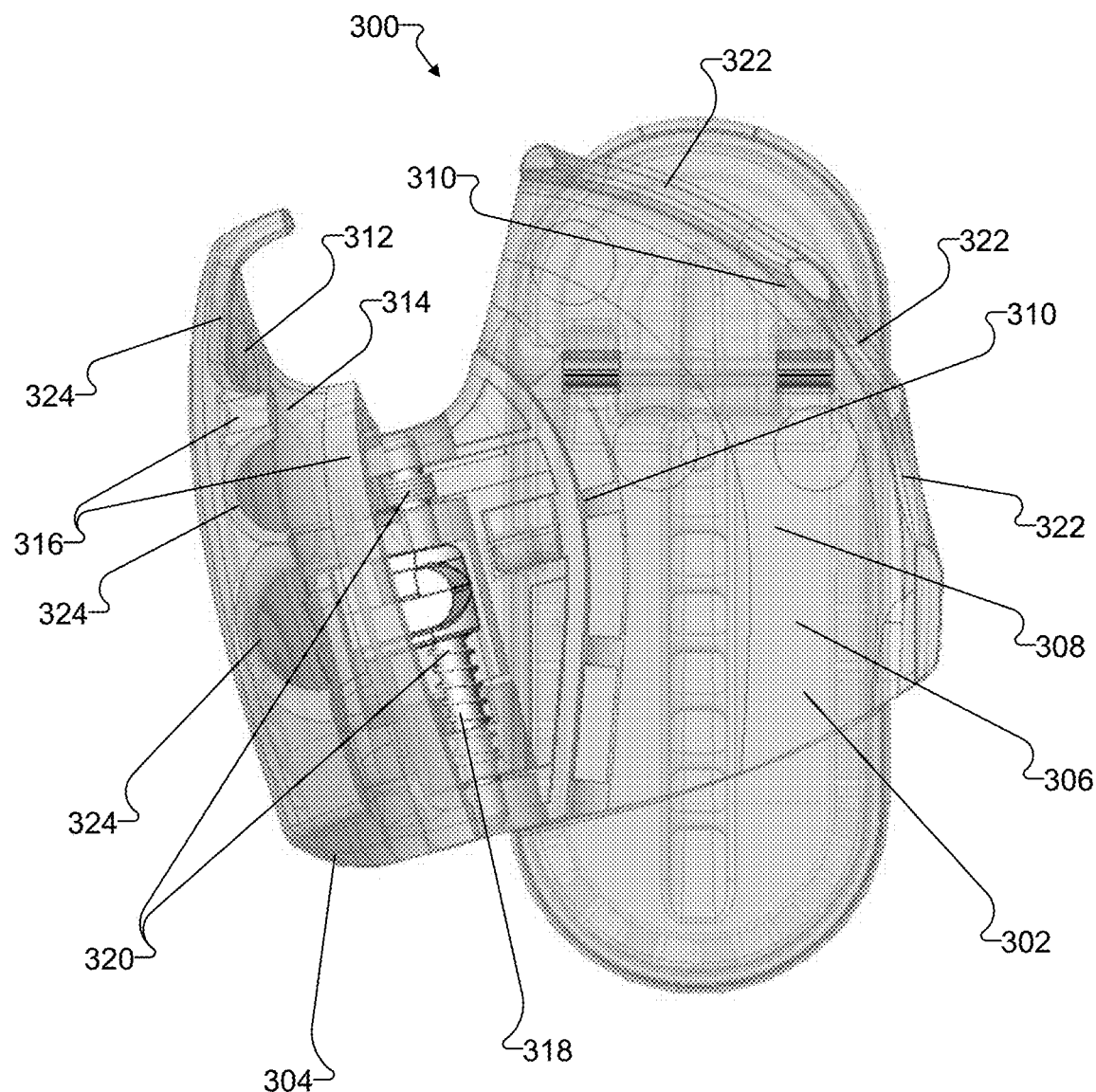
FIG. 3 illustrates an exemplary wearable case according to principles described herein.

FIG. 3 illustrates an exemplary wearable case 300 that may be used to securely cradle sound processor assembly 200 and removably attach to an object. As shown, wearable case 300 includes a cradle member 302 and a cover member 304 that is pivotally connected to cradle member 302.

Cradle member 302 is configured to receive and cradle sound processor assembly 200 when sound processor assembly 200 is placed in wearable case 300. To this end, cradle member 302 has an inner surface 306 that conforms to contours and shapes of an outer surface of portions of sound processor assembly 200. For example, a base surface 308 of inner surface 306 may conform to contours and shapes of rear surface 212 (e.g., portions of rear surface 212 on sound processor module 202 and battery module 204). Additionally, side surfaces 310 of inner surface 306 may conform to contours and shapes of side surfaces 210 of sound processor assembly 200 (e.g., portions of side surfaces 210 on sound processor module 202 and battery module 204).

The shape of inner surface 306 (e.g., base surface 308 and side surfaces 310) of cradle member 302 allows inner surface 306 to securely cradle sound processor assembly 200. For example, base surface 308 conforms to the contours and shapes of rear surface 212 of sound processor assembly 200, thereby holding sound processor assembly 200 in place by restraining backward movement of sound processor assembly 200 (i.e., movement of sound processor assembly 200 toward base surface 308 in a direction normal to rear surface 212 of sound processor assembly 200). Furthermore, side surfaces 310 conform to the contours and shapes of opposing side surfaces 210 of sound processor assembly 200, thereby holding sound processor assembly 200 in place by restraining lateral movement of sound processor assembly 200 (i.e., movement of sound processor assembly 200 in a direction orthogonal to the direction normal to rear surface 212 of sound processor assembly 200).

Cover member 304 is configured to cover and cradle sound processor assembly 200 when sound processor assembly 200 is held by wearable case 300 and cover member 304 is in a closed position. To this end, cover member 304 has an inner surface 312 that conforms to contours and shapes of an outer surface of sound processor assembly 200. For example, a cap surface 314 of inner surface 312 may cover sound processor assembly 200 and conform to contours and shapes of front surface 208 (e.g., portions of front surface 208 on sound processor module 202 and battery module 204). Additionally, side surfaces 316 of inner surface 312 may conform to contours and shapes of side surfaces 210 of sound processor assembly 200 (e.g., portions of side surfaces 210 on sound processor module 202 and battery module 204).

The shape of inner surface 312 (e.g., cap surface 314 and side surfaces 316) of cover member 304 allows inner surface 312 to securely cradle sound processor assembly 200. For example, cap surface 314 conforms to the contours and shapes of front surface 208 of sound processor assembly 200, thereby holding sound processor assembly 200 in place by restraining forward movement of sound processor assembly 200 (i.e., movement of sound processor assembly 200 toward cap surface 314 in a direction normal to front surface 208 of sound processor assembly 200). Furthermore, side surfaces 316 conform to the contours and shapes of opposing side surfaces 210 of sound processor assembly 200, thereby holding sound processor assembly 200 in place by restraining lateral movement of sound processor assembly 200 (i.e., movement of sound processor assembly 200 in a direction orthogonal to the direction normal to front surface 208 of sound processor assembly 200).

As mentioned, cover member 304 is pivotally connected to cradle member 302. Cover member 304 may be pivotally connected to cradle member 302 in any suitable manner. For example, as shown in FIG. 3, cover member 304 is pivotally connected to cradle member 302 by a hinge 318, which allows cover member 304 to pivot from an open position (shown in FIG. 3) to a closed position (shown in FIG. 4).

In some examples, wearable case 300 may include a biasing member to bias cover member 304 to be in either the open position or the closed position. Cover member 304 may be biased in any suitable manner. For example, as shown in FIG. 3, hinge 318 may include springs 320 that push or pull cover member 304 and/or cradle member 302. For example, springs 320 may be configured to bias cover member 304 to the open position. Alternatively, springs 320 may be configured to bias cover member 304 to the closed position. In some examples, wearable case 300 may securely hold sound processor assembly 200 within wearable case 300 by biasing cover member 304 to the closed position to hold sound processor assembly 200 against cradle member 302.

As shown in FIG. 3, side surface 310 of cradle member 302 may include one or more notches 322, and side surface 316 of cover member 304 may include one or more notches 324. When cover member 304 is in a closed position, notches 322 and notches 324 align to define access openings that provide user access to one or more user controls and/or ports, as will be described below in more detail.

Cradle member 302 and cover member 304 may also be configured so as to securely cradle sound processor assembly 200 without fully enclosing sound processor assembly 200. For example, the size (e.g., surface area) of inner surface 306 is smaller than the size (e.g., surface area) of rear surface 212 of sound processor assembly 200, and the size (e.g., surface area) of inner surface 312 of cover member 304 is smaller than the size (e.g., surface area) of front surface 208 of sound processor assembly 200, so that a lower portion of sound processor assembly (e.g., a portion of battery module 204) and an upper portion (e.g., a portion of earhook 206) are not enclosed by wearable case 300. As will be explained below, this configuration allows a user to remove and/or replace battery module 204 and/or earhook 206 while sound processor assembly 200 is secured within wearable case 300.

Figure 4:
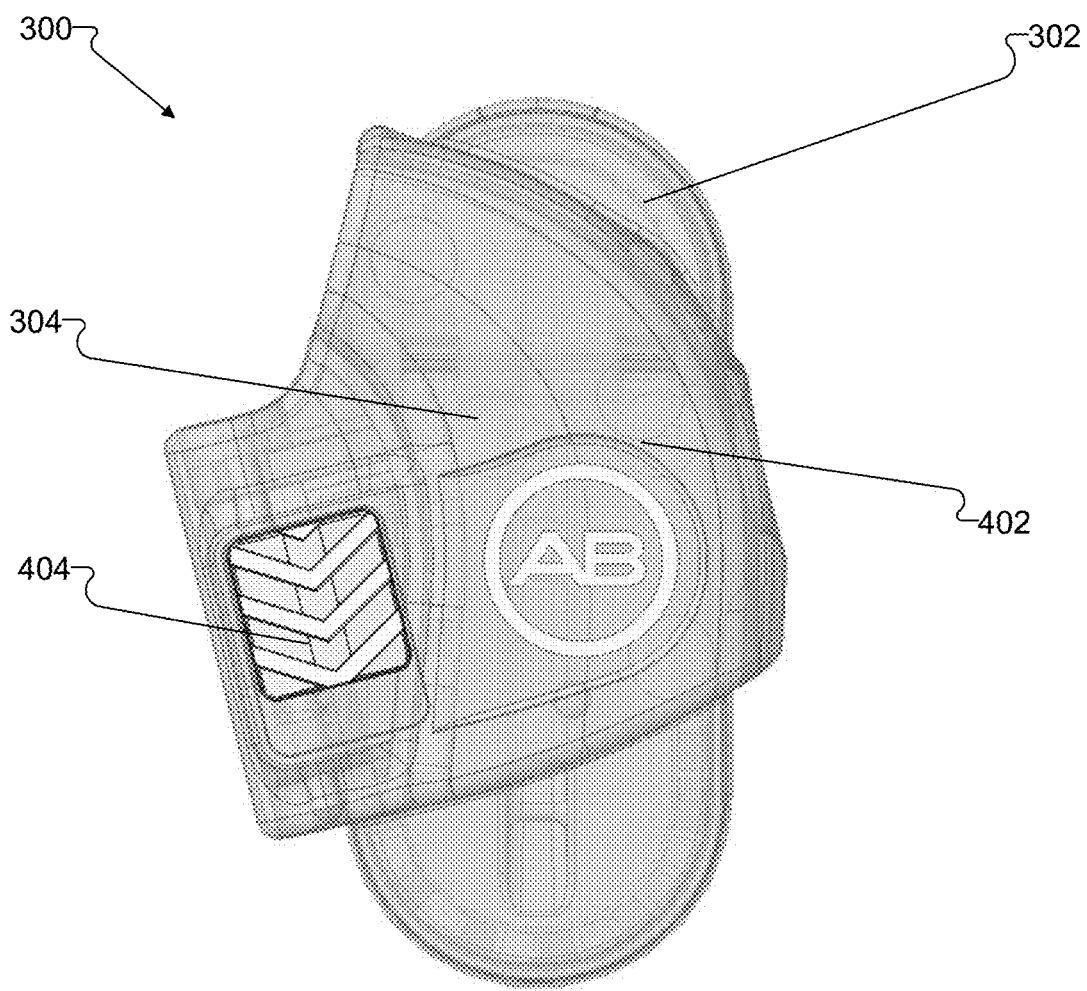
FIG. 4 shows another view of the wearable case of FIG. 3 according to principles described herein.

Referring now to FIG. 4, which shows an exemplary configuration of wearable case 300 in which cover member 304 is in a closed position, cradle member 302 and cover member 304 define a space 402 where sound processor assembly 200 may be accommodated. When cover member 304 is in the closed position, inner surface 312 of cover member 304 faces inner surface 306 of cradle member 302, and side surfaces 316 of cover member 304 are brought into alignment with side surfaces 310 of cradle member 302. When cover member 304 is in the closed position, space 402 is defined by cradle member 302 and cover member 304 between inner surface 306 of cradle member 302 and inner surface 312 of cover member 304. Thus, space 402, defined by the shapes of inner surface 306 of cradle member 302 and inner surface 312 of cover member 304, is shaped to follow the contour and shape of at least a portion of an outer surface of sound processor assembly 200. Thus, when sound processor assembly 200 is accommodated in space 402, as shown in FIGS. 5B and 5C, sound processor assembly 200 is securely cradled by wearable case 300.

In some examples, wearable case 300 may include a locking member that locks cover member 304 in the closed position. Cover member 304 may be locked in the closed position in any suitable manner. For example, as shown in FIG. 4, wearable case 300 includes a locking member 404 disposed on cover member 304. Locking member 404 is configured to lock cover member 304 in the closed position by preventing opening of cover member 304. Locking member 404 may be configured to selectively alternate between an unlocked position and a locked position, and may be implemented by any suitable mechanism (e.g., a lever, a button, a spring clip, etc.) that prevents cover member 304 from opening. Additionally, locking member 404 need not be disposed on cover member 404 but may be disposed on any part or combination of parts of wearable case 300.

FIGS. 5A-5C illustrate placement of sound processor assembly 200 in wearable case 300. As shown in FIG. 5A, while cover member 304 of wearable case 300 is in the open position, sound processor assembly 200 may be placed in cradle member 302. Alternatively, sound processor assembly 200 may be placed in cover member 304.

While sound processor assembly 200 is positioned in cradle member 302 or cover member 304, cover member 304 may be moved from the open position to the closed position by pivoting cover member 304 about hinge 318. As shown in FIGS. 5B and 5C, when cover member 304 is in the closed position over sound processor assembly 200, cradle member 302 and cover member 304 securely cradle sound processor assembly 200 within space 402.

According to this configuration, cradle member 302 and cover member 304 of wearable case 300 form a close-fitting frame around sound processor assembly 200 that restrains movement, in multiple directions, of sound processor assembly 200 within space 402. Accordingly, wearable case 300 (e.g., cradle member 302 and cover member 304) securely cradle sound processor assembly 200 within space 402 in such a way that prevents sound processor assembly 200 from shifting, moving, or jiggling while being held by wearable case 300 but without exerting a force (e.g., putting direct pressure) on sound processor assembly 200.

Additionally, wearable case 300 (e.g., cradle member 302 and cover member 304) may securely cradle sound processor assembly 200 without fully enclosing or surrounding an entire outer surface of sound processor assembly 200. For example, FIGS. 5B and 5C show that wearable case 300 surrounds only a portion of an outer surface of sound processor assembly 200. Therefore, sound processor assembly 200 may be held by wearable case 300 in such a way that one or more portions or components of sound processor assembly 200 are not covered by wearable case 300. For example, as shown in FIG. 5B, a portion of sound processor module 202 is covered by wearable case 300 and a portion of battery module 204 and all of earhook 206 are exposed outside of wearable case 300. Accordingly, various portions of sound processor module 202, battery module 204, and earhook 206 may be exposed outside of wearable case 300, thereby facilitating removal and/or replacement of these components, as will be described below in more detail.

Figure 6A:
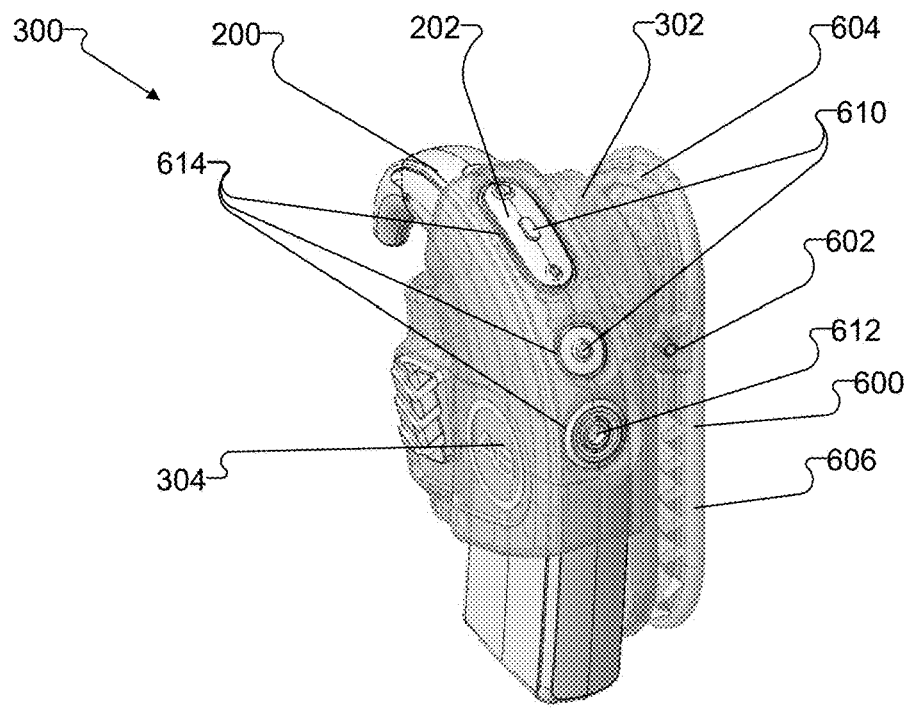
FIGS. 6A and 6B show various views of the wearable case of FIGS. 3 and 4 holding the sound processor assembly of FIG. 2 according to principles described herein.
Figure 6B:
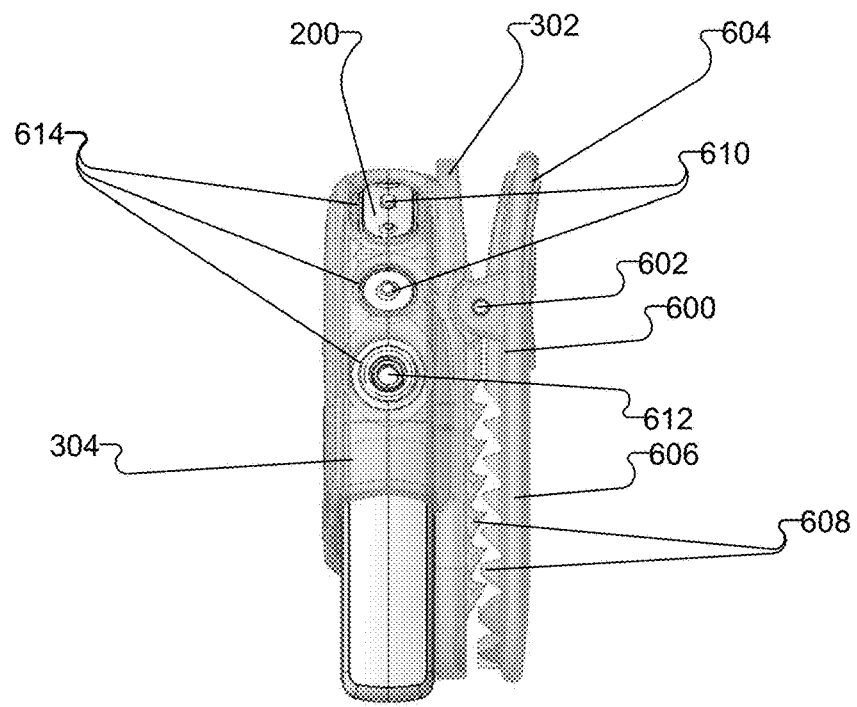

As mentioned above, wearable case 300 may be attached to a user's clothing (e.g., a shirt, a belt, pants, a backpack, etc.), to a part of the user's body, or to any other desired object. To this end, wearable case 300 may include an attachment element configured to attach wearable case 300. The attachment element be implemented by any suitable attachment mechanism. For example, as shown in FIGS. 6A and 6B, wearable case 300 includes a clip 600 pivotally attached to a back surface of wearable case (e.g., a back surface of cradle member 302) by a hinge 602 and biased in a closed position. As shown, clip 600 includes an operation portion 604 on a first side of hinge 602 and an attachment portion 606 on a second side of hinge 602 (e.g., a side that is opposite to the first side). Teeth 608 may be provided on attachment end 606 and on the back surface of cradle member 302 to strengthen the grip of clip 600.

While FIGS. 6A and 6B show an exemplary clip 600, the attachment element may be implemented by any other suitable mechanism or material, including but not limited to a magnetic fastener, a spring clip, a stationary clip, a pin, an adhesive, a hook-and-loop fastener, a snap, a hook or loop (e.g., for fastening to a belt), and the like.

As mentioned above, wearable case 300 may be configured to provide a user with access to various portions of sound processor assembly 200 (e.g., one or more user controls and/or ports) while cover member 304 is in the closed position. For example, sound processor assembly 200 includes buttons 610 and an auxiliary input jack 612 on a side surface of sound processor module 202. Accordingly, as shown in FIGS. 6A and 6B, wearable case 300 includes access openings 614 at positions corresponding to locations of buttons 610 and auxiliary input jack 612 on sound processor assembly 200. Access openings 614 may be partially formed (e.g., notches 322) in side surface 310 of cradle member 302 and may be partially formed (e.g., notches 324) in side surface 316 of cover member 304. Accordingly, when cover member 304 is in the closed position, the partial access openings in side surface 310 of cradle member 302 and side surface 316 of cover member 304 are aligned to form access openings 614, which provide access to buttons 610 and auxiliary input jack 612 while cover member 304 is in the closed position.

Access openings 614 are not limited to the configurations shown and described with reference to FIGS. 6A and 6B. For example, access openings 614 are not limited to being partially formed in side surface 310 of cradle member 302 and side surface 316 of cover member 304, but may be formed in any location on wearable case 300 as may suit a particular implementation. For example, access openings 614 may be formed completely in cradle member 302 and/or cover member 304.

Alternatively to access openings 614, access to user controls (e.g., buttons 610) may be achieved by one or more buttons on wearable case 300 that align and engage with the user controls when operated by a user, thereby allowing a user to indirectly operate the user controls.

Operation and use of wearable case 300 will now be described with reference to FIGS. 7A-7E. FIG. 7A shows a configuration of wearable case 300 where cover member 304 is in the closed position and locking member 404 is in the locked position, thereby locking cover member 304 in the closed position. When locking member 404 is moved to the unlocked position (e.g., by sliding locking member 404 in a downward direction), cover member 304 can pivot between the closed position (shown in FIG. 7B) and the open position (shown in FIG. 7C).

In the open position, inner surface 306 of cradle member 302 and inner surface 312 of cover member 304 are exposed and may receive sound processor assembly 200. For example, as shown in FIG. 7D, sound processor assembly 200 may be placed in cradle member 302. Alternatively, sound processor assembly 200 may be placed in cover member 304.

With sound processor assembly 200 placed in cradle member 302 (or cover member 304), cover member 304 may be closed and locked to secure sound processor assembly 200 within wearable case 300. For example, cover member 304 may be pivoted from the open position (shown in FIG. 7D) to the closed position (shown in FIG. 7E), and locking member may be locked (e.g., by sliding locking member 404 in an upward direction). In the closed and locked position shown in FIG. 7E, sound processor assembly 200 is securely cradled by wearable case 300. For example, cradle member 302 and cover member 304 are in close proximity with the surfaces of sound processor assembly 200 and follow the contours and shapes of the surfaces of sound processor assembly 200. With this configuration, wearable case 300 holds sound processor assembly 200 in such a way that wearable case 300 restrains movement of sound processor assembly 200 within wearable case 300 but without exerting a force on sound processor assembly 200. Furthermore, locking cover member 304 in the closed position prevents accidental opening of cover member 304 and release of sound processor assembly 200. Accordingly, as shown in FIG. 7E, sound processor assembly 200 is securely cradled by wearable case 300.

In some examples locking member 404 may be biased in a locked or unlocked position. For example, locking member 404 may be spring-loaded to bias locking member 404 to the locked position. To illustrate, as shown in FIGS. 7A and 7B, a user may slide locking member 404 from the locked position (shown in FIG. 7A) to the unlocked position (shown in FIG. 7B). After the user releases locking member 404, locking member 404 may spring back to the locked position. According to this configuration, when cover member 304 is moved from the open position (shown in FIG. 7D) to the closed position (shown in FIG. 7E), locking member 404 may spring into the locked position to automatically lock cover member 304 in the closed position.

As mentioned, wearable case 300 (e.g., cradle member 302 and cover member 304) may securely cradle sound processor assembly 200 without fully enclosing or surrounding an entire outer surface of sound processor assembly 200, thereby allowing a user to access and remove certain components of sound processor assembly 200 (e.g., battery module 204 and/or earhook 206).

Figure 8A:
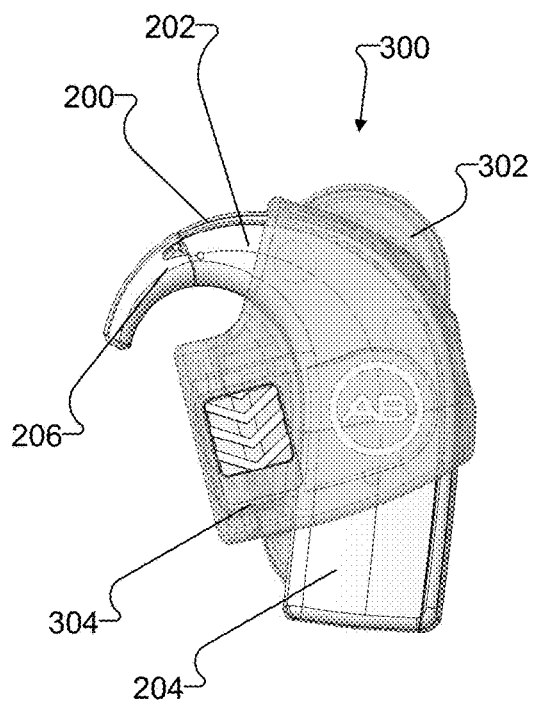
FIGS. 8A-8C show exemplary uses of the wearable case of FIGS. 3 and 4 with various exemplary sound processor assemblies according to principles described herein.

For example, FIG. 8A shows an example where sound processor assembly 200 is securely held by wearable case 300. As shown, portions of sound processor module 202 and battery module 204 and all of earhook 206 are disposed outside of wearable case 300 (i.e., are not accommodated in space 402 between cradle member 302 and cover member 304). Accordingly, a user may remove battery module 204 and/or earhook 206 without removing sound processor assembly 200 from wearable case 300 and without opening cover member 304.

Figure 8B:
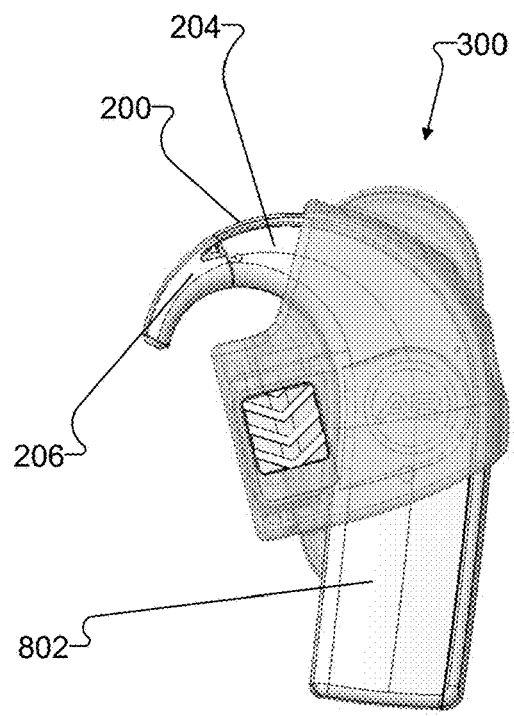

For example, a user may remove battery module 204 (e.g., to recharge battery module 204 or to replace battery module 204 with a different-sized battery module) and replace battery module 204 with another battery module without removing sound processor assembly 200 from wearable case 300. Because a portion of battery module 204 is disposed outside of wearable case 300 when sound processor assembly 200 is held by wearable case 300, wearable case 300 can accommodate battery modules of multiple different sizes. To illustrate, FIG. 8A shows a configuration where wearable case 300 holds sound processor assembly 200 having battery module 204, and FIG. 8B shows a configuration where battery module 204 has been removed and replaced with a larger battery module 802 without removing sound processor assembly 200 from wearable case 300.

Figure 8C:
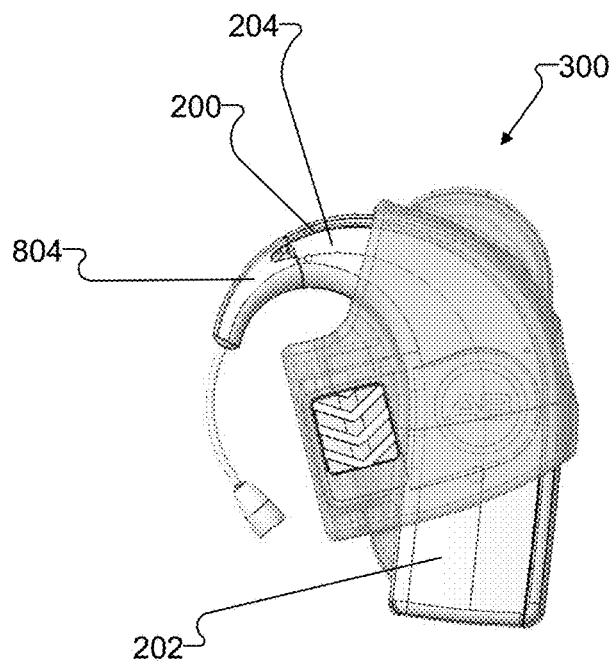

Similarly, a user may access earhook 206 without removing sound processor assembly 200 from wearable case 300. For example, as shown in FIG. 8A, earhook 206 is attached to sound processor module 202 in sound processor assembly 200. Because earhook 206 is disposed outside of wearable case 300 when sound processor assembly 200 is held by wearable case 300, wearable case 300 can accommodate earhooks of multiple different sizes, shapes, or configurations. Accordingly, a user may remove earhook 206 and replace earhook 206 with a different earhook without having to remove sound processor assembly 200 from wearable case 300. To illustrate, FIG. 8A shows a configuration where wearable case 300 holds sound processor assembly 200 with earhook 206 attached to sound processor module 202, and FIG. 8C shows a configuration where earhook 206 has been removed and replaced with a different earhook 804 without removing sound processor assembly 200 from wearable case 300.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:
1. A wearable case for a hearing device, the wearable case comprising:
    a cradle member configured to receive the hearing device; and
    a cover member pivotally connected to the cradle member and configured to selectively pivot between an open position and a closed position;

wherein:
when the cover member is in the closed position, the cradle member and the cover member are configured to securely cradle the hearing device within a space defined by the cradle member and the cover member without fully enclosing an entire surface area of the hearing device, and a portion of a battery module attached to the hearing device is disposed outside the space defined by the cover member and the cradle member, and
when the cover member is in the open position, the hearing device is removable from the cradle member.

2. The wearable case of claim 1, wherein the cradle member and the cover member are configured to securely cradle the hearing device without putting direct pressure on a surface of the hearing device.

3. The wearable case of claim 1, further comprising a clip attached to a back surface of the cradle member, the clip configured to removably attach the wearable case to an object associated with a user of the hearing device.

4. The wearable case of claim 1, wherein an inner surface of the cradle member is shaped to follow contours of a rear surface and side surfaces of the hearing device.

5. The wearable case of claim 4, wherein:
an inner surface of the cover member is shaped to follow contours of a front surface of the hearing device and the side surfaces of the hearing device, and
the inner surface of the cover member holds the hearing device in the cradle member when the cover member is in the closed position.

6. The wearable case of claim 1, wherein the battery module is configured to be selectively attached to the hearing device while the cover member is in the closed position.

7. The wearable case of claim 1, wherein the battery module is configured to be selectively removed from the hearing device while the cover member is in the closed position.

8. The wearable case of claim 1, wherein:
an earhook is configured to be selectively attached to the hearing device while the hearing device is held by the cover member and the cradle member,
a portion of the earhook is disposed outside the space defined by the cover member and the cradle member when the earhook is attached to the hearing device and when the cover member is in the closed position, and
the earhook is configured to be selectively removed from the hearing device while the cover member is in the closed position.

9. The wearable case of claim 1, wherein, when the cover member is in the closed position, an upper portion of the hearing device is disposed outside of the space defined by the cradle member and the cover member.

10. The wearable case of claim 1, wherein an access opening is formed in at least one of the cover member and the cradle member to allow access to a user control provided on the hearing device.

11. The wearable case of claim 1, further comprising a hinge that pivotally connects the cover member to the cradle member.

12. The wearable case of claim 11, wherein the hinge is spring loaded such that the cover member is biased to be in the open position.

13. The wearable case of claim 11, wherein the hinge is spring loaded such that the cover member is biased to be in the closed position.

14. The wearable case of claim 1, wherein:
the cover member includes a locking member that is selectively positionable to selectively be in a locked position and an unlocked position,
when the cover member is in the closed position, the locking member is positioned in the locked position to lock the cover member in the closed position, and
when the cover member in the closed position, the locking member is positioned in the unlocked position to unlock the cover member to allow the cover member to selectively pivot between the closed position and the open position.

15. The wearable case of claim 14, wherein the locking member is spring loaded such that the locking member is biased to be in the locked position such that, when the cover member moves to the closed position, the locking member automatically moves to the locked position to lock the cover member in the closed position.

16. A system comprising:
a hearing device comprising:
a sound processor module; and
a battery module attached to the sound processor module; and
a wearable case comprising:
a cradle member configured to receive the hearing device; and
a cover member pivotally connected to the cradle member and configured to selectively pivot between an open position and a closed position;
wherein:
when the cover member is in the closed position, the cradle member and the cover member are configured to securely cradle the hearing device within a space defined by the cradle member and the cover member without fully enclosing an entire surface area of the battery module, and a portion of the battery module is disposed outside the space defined by the cover member and the cradle member, and
when the cover member is in the open position, the hearing device is removable from the cradle member.

17. The wearable case of claim 16, wherein the cradle member and the cover member are configured to securely cradle the hearing device without putting direct pressure on the hearing device.

18. The wearable case of claim 16, further comprising a clip attached to a back surface of the cradle member, the clip configured to removably attach the wearable case to an object associated with a user of the hearing device.

19. The wearable case of claim 16, wherein an inner surface of the cradle member is shaped to follow contours of a rear surface and side surfaces of the hearing device.

20. A method for securing a hearing device in a wearable case, the wearable case including a cradle member configured to receive the hearing device and a cover member pivotally connected to the cradle member and configured to selectively pivot between an open position and a closed position, the method comprising:
placing the hearing device against the cradle member;
pivoting the cover member from the open position to the closed position to hold the hearing device in the cradle member; and
attaching a battery module to the hearing device while the cover member is in the closed position;
wherein:
when the cover member is in the closed position, the cradle member and the cover member are configured to securely cradle the hearing device within a space defined by the cradle member and the cover member without fully enclosing an entire surface area of the hearing device, and when the cover member is in the open position, the hearing device is removable from the cradle member.

\* \* \* \* \*